United States Patent [19]

Okeda et al.

[11] Patent Number: 5,981,771

[45] Date of Patent: Nov. 9, 1999

[54] RUTHENIUM-OPTICALLY ACTIVE PHOSPHINE COMPLEX, PROCESS FOR THE PREPARATION THEREOF AND PROCESS FOR THE PREPARATION OF OPTICALLY ACTIVE 4-METHYL-2-OXETANONE USING SAME

[75] Inventors: Yoshiki Okeda; Yoji Hori; Toshimitsu Hagiwara, all of Kanagawa, Japan

[73] Assignee: Takasago International Corporation, Tokyo, Japan

[21] Appl. No.: 09/100,755

[22] Filed: Jun. 22, 1998

Related U.S. Application Data

[62] Division of application No. 08/963,619, Nov. 4, 1997.

[30] Foreign Application Priority Data

Nov. 8, 1996 [JP] Japan .................................. 8-311211

[51] Int. Cl.[6] .......................... C07D 305/12; C07F 15/00
[52] U.S. Cl. ........................... 549/328; 549/329; 556/23; 556/136
[58] Field of Search ...................... 549/328, 329; 556/23, 136

[56] References Cited

U.S. PATENT DOCUMENTS 5,412,109  5/1995  Takaya et al. ........................... 549/263

*Primary Examiner*—Porfirio Nazario-Gonzalez
*Attorney, Agent, or Firm*—Sughrue, Mion, Zinn, Macpeak & Seas, PLLC

[57] ABSTRACT

The present invention provides a catalyst which exhibits a high catalytic activity and allows asymmetric reaction in a high asymmetric yield to obtain a reaction product having a high optical purity. The present invention also provides a process for the preparation of an optically active 4-methyl-2-oxetanone having a high optical purity useful as starting material of polymer in a high yield in a short period in the presence of the foregoing catalyst. A novel ruthenium-iodo-optically active phosphine complex is provided, represented by the following general formula (1):

$$Ru\text{—}I_2\text{-}(R^1\text{-}BINAP) \qquad (1)$$

wherein $R^1$-BINAP represents an optically active tertiary phosphine represented by the following general formula (2):

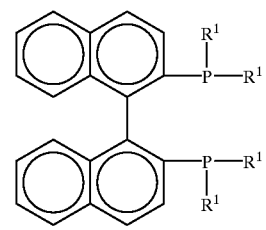

(2)

wherein $R^1$ represents an aryl group which may have a substituent selected from the group consisting of a $C_{1-4}$ lower alkyl group, a $C_{1-4}$ lower alkoxy group, a $C_{1-4}$ lower alkylamino group, and a halogen atom or a $C_{3-8}$ cycloalkyl group.

3 Claims, No Drawings

RUTHENIUM-OPTICALLY ACTIVE PHOSPHINE COMPLEX, PROCESS FOR THE PREPARATION THEREOF AND PROCESS FOR THE PREPARATION OF OPTICALLY ACTIVE 4-METHYL-2-OXETANONE USING SAME

This is a divisional of application Ser. No. 08/963,619 filed Nov. 4, 1997.

FIELD OF THE INVENTION

The present invention relates to a novel ruthenium-iodo-optically active phosphine complex, a process for the preparation thereof and a process for the preparation of an optically active 4-methyl-2-oxetanone in the presence of such a novel ruthenium-iodo-optically active phosphine complex. More particularly, the present invention relates to such a complex to be used as a catalyst for various organic synthesis reactions, particularly asymmetric hydrogenation reaction, a process for the preparation thereof and a process for the preparation of an optically active 4-methyl-2-oxetanone useful as an intermediate for a raw material of a polymer, a synthetic material of medicines, a liquid crystal material, etc., in the industry of organic synthesis in the presence of such a complex.

BACKGROUND OF THE INVENTION

Many transition metal complexes have been heretofore used as catalysts for organic synthesis reaction. In particular, metal complexes made of ruthenium metal and optically active tertiary phosphine have been well known as asymmetric hydrogenation reaction catalysts. Examples of ruthenium-optically-active phosphine complexes containing as a ligand an optically active tertiary phosphine such as 2,2-bis(diphenylphosphino)-1,1-binaphthyl include the following compounds:

$$Ru_xH_yCl_z(\text{tertiary phosphine})_2(A)_p$$

wherein A represents a tertiary amine, with the proviso that if y is 0, x, z and p represent 2, 4 and 1, respectively, and if y is 1, x, z and p represent 1, 1 and 0, respectively (JP-A-61-63690 (The term "JP-A" as used herein means an "unexamined published Japanese patent application"), JP-A-63-135397);

$$[RuH_r(\text{tertiary phosphine})_m]T_n$$

wherein T represents $ClO_4$, $BF_4$ or $PF_6$, with the proviso that if r is 0, m and n represent 1 and 2, respectively, and if r is 1, m and n represent 2 and 1, respectively (JP-A-63-41487, JP-A-63-145492);

$$[RuX_a(Q)_b(\text{tertiary phosphine})]Y_c$$

wherein X represents a halogen atom; Q represents benzene which may have a substituent or acetonitrile; and Y represents a halogen atom, $ClO_4$, $PF_6$, $BPh_4$ (Ph hereinafter represents a phenyl group) or $BF_4$, if Q is benzene which may have a substituent, a, b and c each represent 1, if Q is acetonitrile, when a is 0, b and c represent 4 and 2, respectively, or when a is 1, b and c represent 2 and 1, respectively, and if the benzene having a substituent represented by Q is p-cymene and X and Y each are iodine atom, a, b and c each are 1 or a, b and c are 1, 1 and 3, respectively (JP-A-2-191289, JP-A-5-111639);

(Tertiary phosphine)$_w$Ru(OCOR') (OCOR")

wherein R' and R" each represent a lower alkyl group, a halogenated lower alkyl group, a phenyl group which may have a lower alkyl substituent, an α-aminoalkyl group or an α-aminophenylalkyl group or R' and R" together form an alkylene group; and w represents 1 or 2 (JP-A-62-265293, JP-A-63-145291);

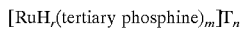

RuJ$_2$(tertiary phosphine)

wherein J represents a chlorine atom, a bromine atom or an iodine atom (R. Noyori et al., J. Am. Chem. Soc., Vol. 109, No. 19, pp. 5856–5859 (1987));

RuG$_2$(tertiary phosphine)

wherein G represents an allyl group or a methallyl group (J. P. Genet et al., Tetrahedron: Asymmetry, Vol. 2, No. 7, pp. 555–567 (1991))

However, even the use of these ruthenium-optically active phosphine complexes has found difficulties in practical use on an industrial basis. For example, these ruthenium-optically active phosphine complexes exhibit an insufficient catalytic activity or asymmetric yield. On the other hand, 4-methyl-2-oxetanone (also referred to as "β-butyrolactone" or "β-methyl-β-propiolactone") has heretofore been used as a raw material of polymers. In recent years, 4-methyl-2-oxetanone has been noted particularly because its optically active form is useful according to JP-A-6-256482, JP-A-6-329768, JP-A-7-53694, JP-A-8-53540 and JP-A-8-127645.

As processes for the preparation of optically active 4-methyl-2-oxetanone there have been reported the following processes:

(a) Process which comprises subjecting 3-bromobutyric acid obtained by adding hydrobromic acid to crotonic acid to optical resolution with an optically active naphthyl ethylamine, and then cyclizing the product (J. Reid Shelton et al., Polymer Letters, Vol. 9, pp. 173–178, 1971; T. Sato et al., Tetrahedron Lett., Vol. 21, pp. 3377–3380, 1980);

(b) Process which comprises reacting an optically active 3-hydroxybutyric acid with triethylorthoacetic acid to obtain an optically active 2-ethoxy-2,6-dimethyl-1,3-dioxane-4-one which is then thermally decomposed (A. Griesbeck et al., Helv. Chim. Acta, Vol. 70, pp. 1320–1325, 1987; R. Breitschuh et al., Chimia, Vol. 44, pp. 216–218, 1990); and (c) Process which comprises reacting an optically active 3-hydroxybutyric acid ester with methanesulfonylchloride for mesylation of the hydroxy group, hydrolyzing the resulting ester, and then reacting with sodium carbonate for condensation cyclization (Y. Zhang et al., Macromolecules, Vol. 23, pp. 3206–3212, 1990).

As a process for the preparation of an optically active 4-methyl-2-oxetanone in the presence of the previously mentioned ruthenium-optically active phosphine complex there has been reported the following process:

(d) Process which comprises the asymmetric hydrogenation of 4-methylene-2-oxetanone (also referred to as "diketene") in an aprotic solvent such as methylene chloride and tetrahydrofuran in the presence of [RuCl[(S)- or (R)-BINAP (benzene)]Cl or Ru$_2$Cl$_4$[(S)- or (R)-BINAP]$_2$(NEt$_3$) [in which BINAP represents 2,2'-bis(diphenylphosphino)-1,1'-binaphthyl, and Et represents an ethyl group] as a catalyst (T. Ohta et al., J. Chem. Soc., Chem. Cmmun., 1725, 1992)

However, these processes have the following disadvantages. In other words, the process (a) requires the use of a special optically active amine as an optically resolving agent in an amount equimolecular with the starting compound. Further, the process (a) subsidiarily produces an undesirable enantiomer in an amount equimolecular with the desired product. Thus, the process (a) is wasteful and economically disadvantageous.

The processes (b) and (c) are disadvantageous in that the optically active 3-hydroxybutyric acid or ester thereof as starting compound can be hardly synthesized. In other words, it is necessary that an optically active poly-3-hydroxybutyric acid ester in which microorganisms propagate themselves be thermally decomposed or 4-methylene-2-oxetanone be converted to acetoacetic acid ester by alcoholysis reaction before asymmetric reduction. This requires many steps and thus complicates the operation.

The process (d) gives solutions to most of the foregoing problems of the processes (a) to (c) but still leave something to be desired. In other words, the process (d) is disadvantageous in that the catalyst used exhibits a low activity, prolonging the reaction time. Further, the resulting product has an optical purity as low as 70 to 92% e.e. As reported in JP-A-6-128245, JP-A-7-188201 and JP-A-7-206885, this process has been improved. However, because of its low catalytic activity, this process leaves something to be desired on an industrial basis.

SUMMARY OF THE INVENTION

It is therefore an object of the present invention to provide a catalyst which exhibits a high catalytic activity and allows asymmetric reaction in a high asymmetric yield to obtain a reaction product having a high optical purity.

It is another object of the present invention to provide a process for the preparation of an optically active 4-methyl-2-oxetanone having a high optical purity useful as a starting material of a polymer in a high yield in a short period in the presence of the foregoing catalyst.

These and other objects of the present invention will become more apparent from the following detailed description and examples.

The inventors made extensive studies of a solution to the foregoing problems. As a result, it was found that a novel ruthenium-iodo-optically active phosphine complex obtained by a relatively simple method exhibits an extremely high catalytic activity and can find wide application as an asymmetric synthesis catalyst. It was also found that the use of this novel ruthenium-iodo-optically active phosphine complex as a catalyst particularly for the asymmetric hydrogenation reaction of 4-methylene-2-oxetanone makes it possible to prepare an optically active 4-methyl-2-oxetanone having a high optical purity in a high yield in a short period of time. Thus, the present invention has been worked out.

The foregoing objects of the present invention are accomplished with a ruthenium-iodo-optically active phosphine complex, represented by the following general formula (1):

Ru—I$_2$-(R$^1$-BINAP)      (1)

wherein R$^1$-BINAP represents an optically active tertiary phosphine represented by the following general formula (2):

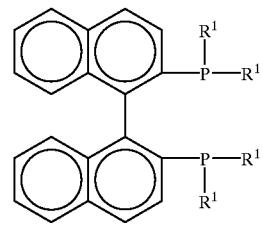

(2)

wherein R$^1$ represents an aryl group which may have a substituent selected from the group consisting of a C$_{1-4}$ lower alkyl group, a C$_{1-4}$ lower alkoxy group, a C$_{1-4}$ lower alkylamino group, and a halogen atom or a C$_{3-8}$ cycloalkyl group.

The ruthenium-iodo-optically active phosphine complex of the present invention shows one or two doublets within a δ range of from −1 to 12 ppm and one or two doublets within a δ range of from 66 to 81 ppm when subjected to $^{31}$P-NMR.

The present invention also concerns a process for the preparation of a ruthenium-iodo-optically active phosphine complex represented by the foregoing general formula (1), which comprises allowing a ruthenium-optically active phosphine complex represented by the following general formula (3):

[RuI(arene) (R$^1$-BINAP)]I      (3)

wherein (arene) represents a hydrocarbon having benzene ring; and R$^1$-BINAP represents an optically active tertiary phosphine represented by the foregoing general formula (2) to undergo reaction in a polar solvent.

The present invention further concerns a process for the preparation of a ruthenium-iodo-optically active phosphine complex, which comprises allowing optically active phosphines represented by the following general formula (4):

[RuI$_2$(arene)]$_2$      (4)

wherein (arene) represents a hydrocarbon having benzene ring and the foregoing general formula (2) to undergo reaction in a polar solvent.

The foregoing objects of the present invention are also accomplished by a process for the preparation of a ruthenium-iodo-optically active phosphine complex, which comprises allowing a ruthenium-optically active phosphine complex represented by the following general formula (5):

Ru(R$^2$COO)$_2$(R$^1$-BINAP)      (5)

wherein R$^2$ represents a hydrogen atom, a lower alkyl group, a halogenated lower alkyl group or an aryl group which may have a lower alkyl substituent; and R$^1$-BINAP represents an optically active tertiary phosphine represented by the foregoing general formula (2) to undergo reaction with hydroborofluoric acid and an inorganic iodide.

The present invention further provides a process for the preparation of an optically active 4-methyl-2-oxetanone, which comprises the asymmetric hydrogenation of 4-methylene-2-oxetanone in the presence of a ruthenium-iodo-optically active phosphine complex represented by the foregoing general formula (1) as a catalyst.

DETAILED DESCRIPTION OF THE INVENTION

The ruthenium-iodo-optically active phosphine complex (hereinafter abbreviated as "Ru—I$_2$-(R$^1$-BINAP)") of the present invention can be obtained by the foregoing three methods. In some detail, the ruthenium-iodo-optically active phosphine complex of the present invention can be obtained by reacting the foregoing ruthenium-phosphine complex (general formula (3)) in a polar solvent with stirring under heating according to the following reaction formula 1 in a reaction vessel in which the air has been replaced by an inert gas such as nitrogen. Alternatively, the ruthenium-iodo-optically active phosphine complex of the present invention can be obtained by reacting the foregoing ruthenium complex (general formula (4)) and phosphine ligand (general formula (2)) in a polar solvent with stirring under heating according to the following reaction formula 2. Further, the ruthenium-iodo-optically active phosphine complex of the present invention can be easily obtained by reacting the foregoing ruthenium-phosphine complex (general formula (5)), hydroborofluoric acid and an inorganic iodide in a solvent with stirring according to the following reaction formula 3.

Reaction formula 1

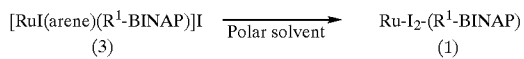

Reaction formula 2

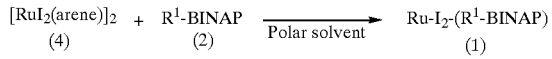

Reaction formula 3

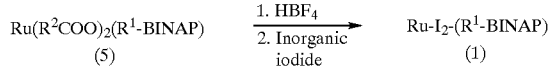

The ruthenium-optically active phosphine complex represented by the foregoing general formula (3) or (5) as a starting material of Ru—I$_2$-(R$^1$-BINAP) of the present invention will be further described. Examples of the aryl group represented by R$^1$ in R$^1$-BINAP represented by the general formula (2) include a phenyl group, a 2-naphthyl group, a substituted phenyl group such as p-substituted phenyl group, m-substituted phenyl group and m-di-substituted phenyl group, and a substituted 2-naphthyl group such as 6-substituted-2-naphthyl group. Examples of the substituents on the phenyl group and naphthyl group include a lower alkyl group (The term "lower" as used herein is meant to indicate "C$_{1-4}$ straight-chain or branched") such as methyl group and tert-butyl group, a lower alkoxy group, a lower alkylamino group, and a halogen atom such as chlorine atom. Particularly preferred examples of the C$_{3-8}$ cycloalkyl group represented by R$^1$ include cyclopentyl group and cyclohexyl group.

Specific examples of the tertiary phosphine represented by R$^1$-BINAP in the ruthenium-optically active phosphine complex represented by the general formula (3) or (5) include the following compounds. Any tertiary phosphine exists both in (R)- and (S)-isomers, but its description is omitted.

(a) 2,2'-Bis(diphenylphosphino)-1,1'-binaphthyl (hereinafter abbreviated as "BINAP")

(b) 2,2'-Bis(di-p-tolylphosphino)-1,1'-binaphthyl (hereinafter abbreviated as "T-BINAP")

(c) 2,2'-Bis[di-(p-tert-butylphenyl)phosphino]-1,1'-binaphthyl (hereinafter abbreviated as "tBu-BINAP")

(d) 2,2'-Bis(di-m-tolylphosphino)-1,1'-binaphthyl (hereinafter abbreviated as "m-T-BINAP")

(e) 2,2'-Bis[di-(3,5-dimethylphenyl)phosphino]-1,1'-binaphthyl (hereinafter abbreviated as "DM-BINAP")

(f) 2,2'-Bis[di-(3,5-di-tert-butylphenyl)phosphino]-1,1'-binaphthyl (hereinafter abbreviated as "DtBu-BINAP")

(g) 2,2'-Bis [di-(p-methoxyphenyl)phosphino]-1,1'-binaphthyl (hereinafter abbreviated as "MeO-BINAP")

(h) 2,2'-Bis[di-(p-chlorophenyl)phosphino]-1,1'-binaphthyl (hereinafter abbreviated as "p-Cl-BINAP")

(i) 2,2'-Bis(di-2-naphthylphosphino)-1,1'-binaphthyl (hereinafter abbreviated as "Naph-BINAP")

(j) 2,2'-Bis(dicyclopentylphosphino)-1,1'-binaphthyl (hereinafter abbreviated as "CpBINAP")

(k) 2,2'-Bis(dicyclohexylphosphino)-1,1'-binaphthyl (hereinafter abbreviated as "CyBINAP")

These tertiary phosphines can be prepared by the method described in JP-A-61-63690, JP-A-3-20290, JP-A-3-255090, JP-A-1-68386, JP-A-4-74192, and JP-A-9-124669.

The ruthenium-optically active phosphine complex represented by the foregoing general formula (3) can be obtained by the method described in JP-A-2-191289 and JP-A-5-111639. Specific examples of the ruthenium-optically active phosphine complex represented by the foregoing general formula (3) thus obtained include the following compounds:

[RuI(benzene)(BINAP)] I
[RuI(benzene)(T-BINAP)] I
[RuI(benzene)(tBu-BINAP)] I
[RuI(benzene)(m-T-BINAP)] I
[RuI(benzene)(DM-BINAP)] I
[RuI(benzene)(DtBu-BINAP)] I
[RuI(benzene)(MeO-BINAP)] I
[RuI(benzene)(p-Cl-BINAP)] I
[RuI(benzene)(Naph-BINAP)] I
[RuI(benzene) (CpBINAP)] I
[RuI(benzene)(CyBINAP)] I
[RuI(p-cymene)(BINAP)] I
[RuI(p-cymene)(T-BINAP)] I
[RuI(p-cymene) (tBu-BINAP)] I
[RuI(p-cymene)(m-T-BINAP))] I
[RuI(p-cymene)(DM-BINAP)] I
[RuI(p-cymene)(DtBu-BINAP)] I
[RuI(p-cymene)(MeO-BINAP)] I
[RuI(p-cymene)(p-Cl-BINAP)] I
[RuI(p-cymene)(Naph-BINAP)] I
[RuI(p-cymene)(CpBINAP)] I
[RuI(p-cymene) (CyBINAP)] I The ruthenium-iodo complex (4) represented by the foregoing general formula (4) can be obtained, e.g., by Zelonka's method (R. A. Zelonka et al., *Can. J. Chem.*, Vol. 50, 3063, 1972). Specific examples of the ruthenium-optically active phosphine complex thus obtained include the following compounds:

[RuI$_2$(benzene)]$_2$
[RuI$_2$(p-cymene)]$_2$

The ruthenium-optically active phosphine complex represented by the foregoing general formula (5) can be obtained by the method described in JP-A-62-265293 and JP-A-63-145291. Specific examples of the ruthenium-optically active phosphine complex thus obtained include the following compounds:

Ru(CH$_3$COO)$_2$(BINAP)
Ru(CF$_3$COO)$_2$(BINAP)
Ru(CH$_3$COO)$_2$(T-BINAP)

Ru(CH$_3$COO)$_2$(tBu-BINAP)
Ru(CH$_3$COO)$_2$(m-T-BINAP)
Ru(CH$_3$COO)$_2$(DM-BINAP)
Ru(CH$_3$COO)$_2$(DtBu-BINAP)
Ru(CH$_3$COO)$_2$(MeO-BINAP)
Ru(CH$_3$COO)$_2$(p-Cl-BINAP)
Ru(CH$_3$COO)$_2$(Naph-BINAP)
Ru(CH$_3$COO)$_2$(CpBINAP)
Ru(CH$_3$COO)$_2$(CyBINAP)

The amount of hydroborofluoric acid to be used as the other starting material in the preparation of Ru—I$_2$-(R$^1$-BINAP) from the ruthenium-optically active phosphine complex represented by the foregoing general formula (5) is preferably from about 2 to 10 mols, particularly from about 4 to 8 mols per mol of the ruthenium-optically active phosphine complex represented by the foregoing general formula (5).

Examples of the inorganic iodide to be used as a starting material in the preparation of Ru—I$_2$-(R$^1$-BINAP) from the ruthenium-optically active phosphine complex represented by the foregoing general formula (5) include iodide of alkaline metal such as sodium iodide (hereinafter referred to as "NaI") and potassium iodide (hereinafter referred to as "KI"), iodide of alkaline earth metal such as calcium iodide, and other metallic iodides such as silver iodide. Particularly preferred among these inorganic iodides are NaI and KI. The amount of the inorganic iodide to be used is preferably from about 4 to 20 mols, particularly from about 6 to 12 mols per mol of the ruthenium-optically active phosphine complex (5).

Examples of the polar solvent to be used in the reaction formulae (1) and (2) shown in FIG. 1 include lower alcohols such as methanol and ethanol, dimethylformamide, dimethyl sulfoxide, dioxane, tetrahydrofuran, and mixture of methanol and methylene chloride.

The temperature at which Ru—I$_2$-(R$^1$-BINAP) of the present invention is prepared according to the reaction formula (1) or (2) shown in FIG. 1 is preferably from about 40° C. to 60° C., particularly from 50° C. to 55° C. The reaction time is preferably from about 10 hours to 40 hours, particularly from about 15 hours to 20 hours.

Examples of the solvent to be used in the reaction formula (3) shown in FIG. 1, i.e., reaction in the presence of the ruthenium-optically active phosphine complex represented by the general formula (5) include mixture of lower alcohol such as methanol and ethanol and organic halide such as methylene chloride, methylene bromide, chloroform and ethylene chloride, and mixture of lower alcohol such as methanol and ethanol and ether such as ethyl ether, diisopropyl ether, dioxane and tetrahydrofuran.

The temperature at which Ru—I$_2$-(R$^1$-BINAP) of the present invention is prepared according to the reaction formula (3) is preferably from about 0° C. to 60° C., particularly room temperature. The reaction time is preferably from about 10 hours to 40 hours, particularly from about 15 hours to 20 hours. After the termination of the reaction, the resulting hydrophobic organic solvent layer may be withdrawn, and then subjected to distillation to remove solvent or drying to obtain the desired Ru—I$_2$-(R$^1$-BINAP).

Ru—I$_2$-(R$^1$-BINAP) thus obtained is presumed to be a complex having a structure formed by separating arene molecule from the compound of the general formula (3) or a complex having a structure formed by replacing carboxyl group in the general formula (5) by iodine atom. Specific examples of Ru—I$_2$-(R$^1$-BINAP) include the following compounds in the form of general formula comprising ruthenium, iodine and optically active tertiary phosphine as minimum constituents of the complex of the present invention. Ru—I$_2$-(R$^1$-BINAP) can be obtained in either (R)- or (S)-isomer depending on the absolute configuration of R$^1$-BINAP (general formula (2)), but its description is omitted.

Ru—I$_2$-(BINAP)
Ru—I$_2$-(T-BINAP)
Ru—I$_2$-(tBu-BINAP)
Ru—I$_2$-(m-T-BINAP)
Ru—I$_2$-(DM-BINAP)
Ru—I$_2$-(DtBu-BINAP)
Ru—I$_2$-(MeO-BINAP)
Ru—I$_2$-(p-Cl-BINAP)
Ru—I$_2$-(Naph-BINAP)
Ru—I$_2$-(CpBINAP)
Ru—I$_2$-(CyBINAP)
Ru—I$_2$-(R$^1$-BINAP) of the present invention thus obtained is a compound which exhibits an extremely high catalytic activity and thus can find wide application as an asymmetric synthesis catalyst. The use of this compound as a catalyst particularly for the asymmetric hydrogenation reaction of 4-methylene-2-oxetanone makes it possible to prepare an optically active 4-methyl-2-oxetanone having a high optical purity in a high yield in a short period of time.

The preparation of an optically active 4-methyl-2-oxetanone in the presence of Ru—I$_2$-(R$^1$-BINAP) of the present invention can be accomplished by the asymmetric hydrogenation of 4-methylene-2-oxetanone as a starting material in the presence of Ru—I$_2$-(R$^1$-BINAP) in a solvent in an atmosphere of nitrogen at a hydrogen pressure of from 5 to 150 kg/cm$^2$ and a temperature range from room temperature to 100° C. in a pressure vessel. 4-Methylene-2-oxetanone to be used as a starting material in this process can be easily synthesized by the thermal decomposition of acetic acid or acetic anhydride according to the method reported by R. J. Clemens (R. J. Clemens et al., *Chem. Rev.*, Vol. 86, pp. 241–318, 1986).

By properly selecting in which isomer Ru—I$_2$-(R$^1$-BINAP) to be used as an asymmetric hydrogenation catalyst occurs, (R)-isomer or (S)-isomer, 4-methyl-2-oxetanone having the desired absolute configuration can be obtained.

In order to effect the preparation of an optically active 4-methyl-2-oxetanone to advantage, Ru—I$_2$-(R$^1$-BINAP) prepared from metallic ruthenium and optically active phosphine in a molar ratio of from 1:1.05 to 1:0.95 may be used. In order to prepare an optically active complex represented by the general formula (3), an optically active phosphine ligand is normally used in an amount of from about 1.05 to 1.2 equivalents per equivalent of ruthenium. The use of an optically active complex prepared from an optically active phosphine ligand in an amount of less than 1.05 equivalents can inhibit the polymerization reaction of 4-methylene-2-oxetanone as a side reaction. If the amount of the optically active phosphine ligand to be used falls below 0.95 equivalent, the amount of the metallic ruthenium to be used is excessive and wasteful.

The amount of Ru—I$_2$-(R$^1$-BINAP) to be used as a catalyst may be normally from about 0.0001 to 0.01 mol, particularly from about 0.0002 to 0.0005 mol per mol of 4-methylene-2-oxetanone as starting material. If the catalyst is used in an amount of less than 0.0001 mol, it cannot exert a sufficient catalytic effect. On the contrary, if the catalyst is used in an amount of more than 0.0005 mol, it is wasteful.

The solvent to be used herein is not specifically limited so far as it is a solvent for use in ordinary asymmetric hydrogenation. Specific examples of the solvent employable herein include straight-chain or cyclic ethers such as diethyl ether, tetrahydrofuran and dioxane, organic halides such as methylene chloride, methylene bromide and dichloroethane, ketones such as acetone, methyl ethyl ketone and methyl butyl ketone, carboxylic acids such as acetic acid and propionic acid, esters such as ethyl acetate, butyl acetate and methyl 3-hydroxybutyrate, aromatic compounds such as toluene and benzene, alcohols such as methanol, ethanol, isopropanol, tert-butyl alcohol and 1,3-butanediol, and mixture thereof. In order to raise the rate of asymmetric hydrogenation reaction, water may be added to the foregoing solvent in an amount of about 1%.

The temperature and time of asymmetric hydrogenation reaction depend on the kind of the catalyst used and other reaction conditions. In practice, however, the asymmetric hydrogenation reaction may be effected at a temperature of from room temperature to 100° C., particularly from about 30° C. to 60° C. for about 0.5 to 40 hours. The hydrogen pressure is preferably from about 5 to 150 kg/cm$^2$, particularly from about 20 to 100 kg/cm$^2$. After the termination of the reaction, the resulting product may be subjected to purification such as distillation of solvent to obtain the desired optically active 4-methyl-2-oxetanone.

The present invention will be further described in the following examples and comparative examples, but the present invention should not be construed as being limited thereto. In the following examples, the measurement of the physical properties of the compounds obtained was effected by means of the following apparatus:

$^{31}$P-NMR spectrum:
   Type AM-400 NMR spectroscope (available from Bruker, Inc.)
   External standard substance; 85% phosphoric acid
   Solvent; Chloroform
(Measurement of optical purity)
   Gas chromatograph: HEWLETT PACKARD 5890 SERIES II
   Optically active column; Chiraldex G-TA 30 m (available from ASTEC Corp.)

EXAMPLE 1

Preparation of Ru—I$_2$-[(S)-BINAP]

The air in a 80 ml Schlenk tube was replaced by nitrogen. Into the tube were charged 1.0 g (1.02 mmol) of [RuI$_2$(p-cymene)]$_2$, 1.29 g (2.07 mmol) of (S)-BINAP and 40 ml of methanol which were then stirred at a temperature of 55° C. for 17 hours. As a result, 2.20 g (yield: 96%) of the desired compound was obtained.

$^{31}$P-NMR: δ: 4.0 (d, J=39 Hz), 7.3 (d, J=35 Hz), 75.8 (d, J=35 Hz), 77.2 (d, J=39 Hz)

EXAMPLE 2

Preparation of Ru—I$_2$-[(S)-T-BINAP]

The air in a 300 ml of a reaction vessel was replaced by nitrogen. Into the reaction vessel were charged 1.80 g (1.989 mmol) of Ru(CH$_3$COO)$_2$[(S)-T-BINAP], 30 ml of methylene chloride, 2.5 ml of methanol and 2.49 g (11.91 mmol) of a 42% hydroborofluoric acid which were then stirred at room temperature for 3 hours. Thereafter, 2.37 g (15.81 mmol) of sodium iodide was dissolved in 17 ml of deaerated water in an atmosphere of nitrogen. The solution was then added to the foregoing mixture. The mixture was then stirred at room temperature for 15 hours. The resulting methylene chloride phase was withdrawn by syringe, and then washed with 20 ml of deaerated water. Methylene chloride was then distilled off under reduced pressure. The resulting complex was then dried at a temperature of 40° C. under reduced pressure for 4 hours to obtain 2.07 g (yield: 100.7%) of the desired compound Ru—I$_2$-[(S)-T-BINAP].

$^{31}$P-NMR: δ: 1.8 (d, J=32 Hz), 4.6 (d, J=35 Hz), 75.0 (d, J=35 Hz), 76.4 (d, J=32 Hz)

EXAMPLE 3

Preparation of Ru—I$_2$-[(S)-T-BINAP]

The air in a 100 ml reaction vessel was replaced by nitrogen. Into the reaction vessel were charged 1.64 g (1.404 mmol) of (RuI (p-cymene) ((S)-T-BINAP]I and 90 ml of methanol which were then stirred at a temperature of 55° C. for 15 hours. As a result, 1.52 g (yield: 93%) of the desired compound was obtained.

$^{31}$P-NMR: δ: 1.8 (d, J=32 Hz), 4.6 (d, J=35 Hz), 75.0 (d, J=35 Hz), 76.5 (d, J=32 Hz)

EXAMPLE 4

Preparation of Ru—I$_2$-[(S)-T-BINAP]

The air in a 80 ml Schlenk tube was replaced by nitrogen. Into the tube were charged 1.0 g (1.02 mmol) of [RuI$_2$(p-cymene)]$_2$, 1.41 g (2.07 mmol) of (S)-T-BINAP and 40 mg of methanol which were then stirred at a temperature of 55° C. for 16 hours. As a result, 2.35 g (yield: 98%) of the desired compound was obtained.

$^{31}$P-NMR: 5: 1.8 (d, J=32 Hz), 4.6 (d, J=35 Hz), 75.0 (d, J=35 Hz), 76.4 (d, J=32 Hz)

EXAMPLE 5

Preparation of Ru—I$_2$-[(S)-tBu-BINAP]

The air in a 80 ml Schlenk tube was replaced by nitrogen. Into the tube were charged 0.34 g (0.348 mmol) of [RuI$_2$(p-cymene)]$_2$, 0.59 g (0.696 mmol) of (S)-tBu-BINAP and 15 ml of methanol which were then stirred at a temperature of 55° C. for 16 hours. As a result, 0.90 g (yield: 97%) of the desired compound was obtained.

$^{31}$P-NMR: δ: 0.4 (d, J=32 Hz), 11.9 (d, J=37 Hz), 67.0 (d, J=37 Hz), 74.0 (d, J=32 Hz)

EXAMPLE 6

Preparation of Ru—I$_2$-[(S)-DM-BINAP]

The air in a 80 ml Schlenk tube was replaced by nitrogen. Into the tube were charged 0.50 g (0.511 mmol) of [RuI$_2$(p-cymene))$_2$, 0.76 g (1.03 mmol) of (S)-DM-BINAP and 20 ml of methanol which were then stirred at a temperature of 55° C. for 20 hours. As a result, 1.20 g (yield: 96%) of the desired compound was obtained.

$^{31}$P-NMR: δ: 1.8 (d, J=41 Hz), 78.0 (d, J=41 Hz)

EXAMPLE 7

Preparation of Ru—I$_2$-[(S)-MeO-BINAP]

The air in a 80 ml Schlenk tube was replaced by nitrogen. Into the tube were charged 0.40 g (0.409 mmol) of [RuI$_2$(p-cymene))$_2$, 0.614 g (0.827 mmol) of (S)-MeO-BINAP and 20 ml of methanol which were then stirred at a temperature of 55° C. for 18 hours. As a result, 1.00 g (yield: 99%) of the desired compound was obtained.

$^{31}$P-NMR: δ: −0.1 (d, J=33 Hz), 3.0 (d, J=36 Hz), 73.0 (d, J=36 Hz), 74.9 (d, J=33 Hz)

EXAMPLE 8

Preparation of Ru—$I_2$-[(S)-Naph-BINAP]

The air in a 80 ml Schlenk tube was replaced by nitrogen. Into the tube were charged 0.3 g (0.307 mmol) of [$RuI_2$(p-cymene)]$_2$, 0.51 g (0.620 mmol) of (S)-Naph-BINAP and 20 ml of dimethylformamide which were then stirred at a temperature of 55° C. for 16 hours. As a result, 0.80 g (yield: 99%) of the desired compound was obtained.

$^{31}$P-NMR: δ: 9.9 (br), 80.8 (br)

EXAMPLE 9

Preparation of (R)-4-methyl-2-oxetanone

Into a 500 ml stainless steel autoclave were charged in an atmosphere of nitrogen 44.12 mg (0.0397 nmol) of Ru—$I_2$-[(S)-BINAP], 20.6 g (245.2 mmol) of 4-methylene-2-oxetaone, 160 ml of tetrahydrofuran and 0.9 ml of deaerated water which were then stirred at a reaction temperature of 40° C. under a hydrogen pressure of 50 kg/cm² for 40 hours. The resulting reaction solution was then subjected to distillation by a Claisen distillation apparatus to obtain 13.3 g (yield: 63.1%) of a fraction having a boiling point of from 71° C. to 73° C./29 mmHg. This reaction showed a conversion of 64.7% and a catalytic activity of 4,000 as calculated in turnover. As a result of comparison with the standard by gas chromatography, the resulting reaction product was identified as 4-methyl-2-oxetanone. Gas chromatography (GC) of the reaction product through an optically active column (Cthiraldex G-Ta 30 m) available from ASTEC Corp. showed that the reaction product is (R) absolute configuration and an optical purity of 94.9% e.e.

EXAMPLE 10

Preparation of (R)-4-methyl-2-oxetanone

The reaction procedure of Example 9 was followed except that 61.80 mg (0.0529 mmol) of Ru—$I_2$-[(S)-T-BINAP] and 20.0 g (238.1 mmol) of 4-methylene-2-oxetanone were used. As a result, 18.8 g (yield: 92%) of the desired compound was obtained. This reaction showed a conversion of 100% and a catalytic activity of 4,500 as calculated in terms of turnover. The reaction product showed (R) absolute configuration and an optical purity of 93.6% e.e.

EXAMPLE 11

Preparation of (R)-4-methyl-2-oxetanone

The reaction procedure of Example 9 was followed except that 3.02 mg (0.0397 mmol) of Ru—$I_2$-[(S)-tBu-BINAP] and 20.2 g (240.5 mmol) of 4-methylene-2-oxetanone were used. As a result, 12.3 g (yield: 59.5%) of the desired compound was obtained. This reaction showed a conversion of 61.1% and a catalytic activity of 3,700 as calculated in terms of turnover. The reaction product showed (R) absolute configuration and an optical purity of 94.6% e.e.

EXAMPLE 12

Preparation of (R)-4-methyl-2-oxetanone

The reaction procedure of Example 9 was followed except that 48.6 mg (0.0397 mmol) of Ru—$I_2$-[(S)-DM-BINAP] and 20.5 g (244.0 mmol) of 4-methylene-2-oxetanone were used. As a result, 11.3 g (yield: 53.8%) of the desired compound was obtained. This reaction showed a conversion of 55.3% and a catalytic activity of 3,400 as calculated in terms of turnover. The reaction product showed (R) absolute configuration and an optical purity of 95.1% e.e.

EXAMPLE 13

Preparation of (R)-4-methyl-2-oxetanone

The reaction procedure of Example 9 was followed except that 48.9 mg (0.0397 mmol) of Ru—$I_2$-[(S)-MeO-BINAP] and 19.2 g (228.6 mmol) of 4-methylene-2-oxetanone were used. As a result, 10.6 g (yield: 53.9%) of the desired compound was obtained. This reaction showed a conversion of 55.5% and a catalytic activity of 3,200 as calculated in terms of turnover. The reaction product showed (R) absolute configuration and an optical purity of 93.6% e.e.

EXAMPLE 14

Preparation of (R)-4-methyl-2-oxetanone

The reaction procedure of Example 9 was followed except that 57.0 mg (0.0434 mmol) of Ru—$I_2$-[(S)-Naph-BINAP] and 20.1 g (239.3 mmol) of 4-methylene-2-oxetanone were used. As a result, 19.1 g (yield: 93%) of the desired compound was obtained. This reaction showed a conversion of 100% and a catalytic activity of 5,500 as calculated in terms of turnover. The reaction product showed (R) absolute configuration and an optical purity of 94.7% e.e.

COMPARATIVE EXAMPLE 1

Preparation of (R)-4-methyl-2-oxetanone

A ruthenium-iodo-optically active phosphine complex described in JP-A-7-206885 was prepared. Using this complex as a catalyst, an optically active 4-methyl-2-oxetanone was prepared. In some detail, into a 300-ml reaction vessel in which the air within had been replaced by nitrogen were charged 0.57 g (0.632 mmol) of $Ru_2Cl_4$[(S)-T-BINAP]$_2NEt_3$, 0.95 g (6.34 mmol) of NaI, 2.0 mg (0.0063 mmol) of $(C_4H_9)_4NBr$, 50 ml of methylene chloride and 20 ml of distilled water which were then stirred at room temperature for 44 hours. After the termination of the reaction, the resulting methylene chloride phase was withdrawn by syringe. Methylene chloride was then distilled off under reduced pressure. The resulting complex was then dried at a temperature of 50° C. under reduced pressure for 4 hours to obtain 0.65 g of Ru—I-[(S)-T-BINAP].

The reaction procedure of Example 9 was followed except that 41.0 mg (0.0397 mmol) of the complex Ru—I-[(S)-T-BINAP] was measured out and used and 20.0 g (238.1 mmol) of 4-methylene-2-oxetanone was used. As a result, 10.0 g (yield: 48.8%) of the desired compound was obtained. This reaction showed a conversion of 50.0% and a catalytic activity of 3,000 as calculated in terms of turnover. The reaction product showed (R) absolute configuration and an optical purity of 93.2% e.e.

COMPARATIVE EXAMPLE 2

Preparation of (R)-4-methyl-2-oxetanone

The reaction procedure of Example 9 was followed except that 139.0 mg (0.119 mmol) of (RuI(p-cymene)((S)-T-BINAP]I and 20.0 g (238.1 mmol) of 4-methylene-2-oxetanone were used. As a result, 10.0 g (yield: 48.8%) of the desired compound was obtained. This reaction showed a conversion of 50.0% and a catalytic activity of 1,000 as calculated in terms of turnover. The reaction product showed (R) absolute configuration and an optical purity of 92.6% e.e.

COMPARATIVE EXAMPLE 3

Preparation of (R)-4-methyl-2-oxetanone

The reaction procedure of Example 9 was followed except that 215.5 mg (0.238 mmol) of $Ru(CH_3COO)_2$[(S)-T-

BINAP] and 20.0 g (238.1 mmol) of 4-methylene-2-oxetanone were used. As a result, 12.0 g (yield: 58.6%) of the desired compound was obtained. This reaction showed a conversion of 59.9% and a catalytic activity of 600 as calculated in terms of turnover. The reaction product showed (R) absolute configuration and an optical purity of 93.3% e.e.

The catalytic activity (turnover) of Examples 9 to 14 and Comparative Examples 1 to 3 and the steric configuration and optical purity (% e.e.) of 4-methyl-2-oxetanone are together set forth in Table 1.

TABLE 1

| Example No. | Catalyst | Catalytic activity (turnover) | Steric configuration and optical purity (%e.e.) of 4-methyl-2-oxetanone |
|---|---|---|---|
| Example 9 | Ru-I$_2$-[(S)-BINAP] | 4,000 | (R)-isomer 94.9 |
| Example 10 | Ru-I$_2$-[(S)-T-BINAP] | 4,500 | (R)-isomer 93.6 |
| Example 11 | Ru-I$_2$-[(S)-tBu-BINAP] | 3,700 | (R)-isomer 94.8 |
| Example 12 | Ru-I$_2$-[(S)-DM-BINAP] | 3,400 | (R)-isomer 95.1 |
| Example 13 | Ru-I$_2$-[(S)-MeO-BINAP] | 3,200 | (R)-isomer 93.6 |
| Example 14 | Ru-I$_2$-[(S)-Naph-BINAP] | 5,500 | (R)-isomer 94.7 |
| Comparative Example 1 | Ru-I-[(S)-T-BINAP] | 3,000 | (R)-isomer 93.2 |
| Comparative Example 2 | [RuI(p-cymene)((S)-T-BINAP]I | 1,000 | (R)-isomer 92.6 |
| Comparative Example 3 | Ru(CH$_3$COO)$_2$[(S)-T-BINAP] | 600 | (R)-isomer 93.3 |

These results show that the examples of the present invention comprising the use of the complex of the present invention Ru—I$_2$-(R$^1$-BINAP) allow the progress of reaction at a much higher turnover than the comparative examples comprising the use of ruthenium-optically active phosphine complexes which have heretofore been known. Further, the examples of the present invention can provide a product having a high optical purity.

The ruthenium-iodo-optically active phosphine complexes obtained according to the preparation process of the present invention exhibit an extremely high catalytic activity and allow asymmetric reaction in a high asymmetric yield to obtain a reaction product having a high optical purity. Thus, these ruthenium-iodo-optically active phosphine complexes can find wide application as economically favorable asymmetric synthesis catalysts. The use of such a complex as a catalyst particularly for the asymmetric hydrogenation reaction of 4-methylene-2-oxetanone makes it possible to prepare an optically active 4-methyl-2-oxetanone having a high optical purity in a high yield in a short period of time.

While the invention has been described in detail and with reference to specific embodiments thereof, it will be apparent to one skilled in the art that various changes and modifications can be made therein without departing from the spirit and scope thereof.

What is claimed is:

1. A process for the preparation of an optically active 4-methyl-2-oxetanone, which comprises the asymmetric hydrogenation of 4-methylene-2-oxetanone in the presence of as a catalyst a ruthenium-iodo-optically active phosphine complex represented by the following general formula (1):

Ru—I$_2$-(R$^1$-BINAP)  (1)

wherein R$^1$-BINAP represents an optically active tertiary phosphine represented by the following general formula (2):

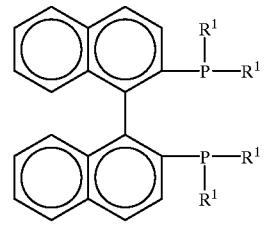

(2)

wherein R$^1$ represents an aryl group which may have a substituent selected from the group consisting of a C$_{1-4}$ lower alkyl group, a C$_{1-4}$ lower alkoxy group, a C$_{1-4}$ lower alkylamino group, and a halogen atom or a C$_{3-8}$ cycloalkyl group.

2. The process for the preparation of an optically active 4-methyl-2-oxetanone according to claim 1, wherein said ruthenium-iodo-optically active phosphine complex is obtained by any one of the following three preparation processes (A)–(C):

(A) a process which comprises allowing a ruthenium-optically active phosphine complex represented by the following general formula (3):

RuI(arene)(R$^1$-BINAP)]I  (3)

wherein (arene) represents a hydrocarbon having benzene ring: and R'-BINAP is as earlier defined: to undergo reaction in a polar solvent;

(B) a process which comprises allowing an optically active phosphine represented by the following general formula (4):

[RuI$_2$(arene)]$_2$  (4)

wherein (arene) represents a hydrocarbon having benzene ring and the optically active tertiary phosphine represented by the general formula (2) to undergo reaction in a polar solvent; or (C) a process which comprises allowing a ruthenium-optically active phosphine complex represented by the following general formula (5):

Ru(R²COO)₂(R¹-BINAP)     (5)

wherein R² represents a hydrogen atom, a lower alkyl group, a halogenated lower alkyl group or an aryl group which may have a lower alkyl substituent, and R¹-BINAP is as earlier defined;

to undergo reaction with hydroborofluoric acid and an inorganic iodide.

3. The process for the preparation of an optically active 4-methyl-2-oxetanone according to claim 1, wherein said ruthenium-iodo-optically active phosphine complex shows one or two doublets within a δ range of from −1 to 12 ppm and one or two doublets within a δ range of from 66 to 81 ppm when subjected to $^{31}$P-NMR.

* * * * *